(12) United States Patent
Mahajan et al.

(10) Patent No.: US 11,058,469 B2
(45) Date of Patent: Jul. 13, 2021

(54) MINIMAL SHOCK SET SCREW

(71) Applicants: Ajay Mahajan, North Canton, OH (US); Jason King, North Canton, OH (US); Tim Paul, Hiram, OH (US)

(72) Inventors: Ajay Mahajan, North Canton, OH (US); Jason King, North Canton, OH (US); Greg Norman, Wadsworth, OH (US); Tim Paul, Hiram, OH (US)

(73) Assignee: The University of Akron, Akron, OH (US)

( * ) Notice: Subject to any disclaimer, the term of this patent is extended or adjusted under 35 U.S.C. 154(b) by 622 days.

(21) Appl. No.: 15/116,363

(22) PCT Filed: Dec. 15, 2014

(86) PCT No.: PCT/US2014/070309
§ 371 (c)(1),
(2) Date: Aug. 3, 2016

(87) PCT Pub. No.: WO2015/089501
PCT Pub. Date: Jun. 18, 2015

(65) Prior Publication Data
US 2016/0367303 A1     Dec. 22, 2016

Related U.S. Application Data

(60) Provisional application No. 61/915,572, filed on Dec. 13, 2013.

(51) Int. Cl.
*A61B 17/86*     (2006.01)
*A61B 90/00*     (2016.01)
(Continued)

(52) U.S. Cl.
CPC ...... *A61B 17/8615* (2013.01); *A61B 17/7001* (2013.01); *A61B 17/86* (2013.01);
(Continued)

(58) Field of Classification Search
CPC ............... A61B 2090/037; A61B 17/86; A61F 2250/0071; A61F 2002/30561; F16B 31/021; B25B 23/1415
See application file for complete search history.

(56) References Cited

U.S. PATENT DOCUMENTS

| | | | | |
|---|---|---|---|---|
| 1,300,275 A | * | 4/1919 | Johnson | B25B 13/48 81/120 |
| 3,498,174 A | * | 3/1970 | Hatter | F16B 31/021 411/5 |

(Continued)

OTHER PUBLICATIONS

International Searching Authority; International Search Report; 4 pages.
International Searching Authority; Written Opinion; 6 pages.

*Primary Examiner* — David W Bates
(74) *Attorney, Agent, or Firm* — Renner, Kenner, Grieve, Bobak, Taylor & Weber

(57) ABSTRACT

The present invention is generally directed to a reduced shock breakaway screw for use with medical implants and the like having improved solid wall geometry in the breakaway area between the upper and lower portions of the set screw. This improved geometry serves to slow down the fracturing process during shearing, thereby increasing the proportion of energy dissipated as heat from plastic deformation of the material to the amount of energy released as kinetic energy from elastic rebound.

7 Claims, 10 Drawing Sheets

(51) Int. Cl.
*A61B 17/88* (2006.01)
*A61B 17/70* (2006.01)

(52) U.S. Cl.
CPC ...... *A61B 17/8605* (2013.01); *A61B 17/8875* (2013.01); *A61B 2090/037* (2016.02)

(56) References Cited

U.S. PATENT DOCUMENTS

| | | | | |
|---|---|---|---|---|
| 4,018,111 | A * | 4/1977 | Goldhaber | F16B 23/0046 81/436 |
| 4,109,691 | A * | 8/1978 | Wilson | F16B 31/027 81/119 |
| 4,342,477 | A * | 8/1982 | McClure | B65D 33/34 24/135 N |
| 4,838,746 | A * | 6/1989 | Giannuzzi | F16B 19/04 411/5 |
| 4,840,529 | A * | 6/1989 | Phillips | F01L 1/20 403/320 |
| 4,884,929 | A * | 12/1989 | Smith | B64D 45/02 411/3 |
| 4,923,471 | A * | 5/1990 | Morgan | A61B 17/8085 606/285 |
| 5,120,168 | A * | 6/1992 | Padula | F16B 31/021 411/5 |
| 5,154,557 | A * | 10/1992 | Houck | F16B 31/02 411/6 |
| 5,312,255 | A * | 5/1994 | Bauer | A61C 8/0012 433/173 |
| 5,697,743 | A * | 12/1997 | Parker | F16B 23/00 411/5 |
| 5,697,929 | A * | 12/1997 | Mellinger | A61B 17/7001 411/5 |
| 5,784,738 | A * | 7/1998 | Updike | E01D 15/124 14/2.4 |
| 6,004,349 | A * | 12/1999 | Jackson | A61B 17/7032 411/3 |
| 6,036,421 | A * | 3/2000 | Demaray | F16B 43/00 411/169 |
| 6,059,786 | A * | 5/2000 | Jackson | A61B 17/7032 606/305 |
| 6,193,719 | B1 * | 2/2001 | Gournay | A61B 17/7049 411/5 |
| 6,224,596 | B1 * | 5/2001 | Jackson | A61B 17/7032 411/5 |
| 6,454,772 | B1 * | 9/2002 | Jackson | A61B 17/7032 606/306 |
| 6,478,795 | B1 * | 11/2002 | Gournay | A61B 17/7049 606/246 |
| 6,554,831 | B1 * | 4/2003 | Rivard | A61B 17/7035 606/253 |
| 6,726,687 | B2 * | 4/2004 | Jackson | A61B 17/7032 606/270 |
| 6,743,233 | B1 * | 6/2004 | Baldwin | A61B 17/0401 606/232 |
| 6,997,927 | B2 * | 2/2006 | Jackson | A61B 17/7032 606/273 |
| 7,425,112 | B2 * | 9/2008 | Nowak, Jr. | F16B 23/0069 411/402 |
| 7,980,801 | B2 * | 7/2011 | Kawano | F16B 33/004 411/402 |
| 8,273,109 | B2 * | 9/2012 | Jackson | F16B 35/047 606/273 |
| 8,992,544 | B2 * | 3/2015 | Basing | A61B 17/8888 606/104 |
| 9,375,242 | B2 * | 6/2016 | Worcel | A61B 17/8047 |
| 2002/0072750 | A1 | 6/2002 | Jackson | |
| 2003/0198528 | A1 * | 10/2003 | Onishi | F16B 31/021 411/2 |
| 2004/0039383 | A1 | 2/2004 | Jackson | |
| 2005/0267477 | A1 | 12/2005 | Jackson | |
| 2007/0209487 | A1 * | 9/2007 | Helstern | F16B 31/021 81/471 |
| 2007/0243035 | A1 * | 10/2007 | Pratt | F16B 31/021 411/15 |
| 2009/0041559 | A1 * | 2/2009 | Tedeschi | F16B 31/021 411/2 |
| 2011/0106179 | A1 * | 5/2011 | Prevost | A61B 17/7032 606/308 |
| 2011/0150596 | A1 * | 6/2011 | Wolodko | F16D 9/08 411/5 |
| 2012/0207563 | A1 * | 8/2012 | Schaeffer | F16B 33/008 411/3 |
| 2013/0131737 | A1 * | 5/2013 | Cheng | A61B 17/863 606/316 |
| 2013/0197585 | A1 * | 8/2013 | Jackson | A61B 17/7035 606/278 |
| 2014/0236237 | A1 * | 8/2014 | Mahajan | A61B 17/863 606/270 |
| 2020/0093565 | A1 * | 3/2020 | Birchler | A61B 17/8635 |
| 2020/0166068 | A1 * | 5/2020 | Sailer | F16B 31/021 |

* cited by examiner

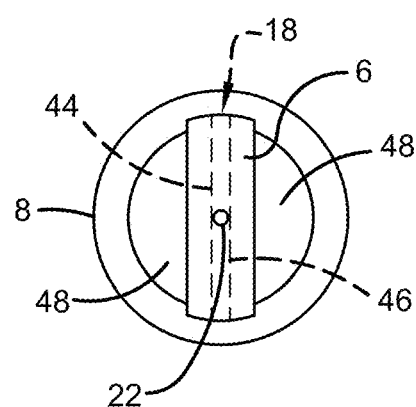
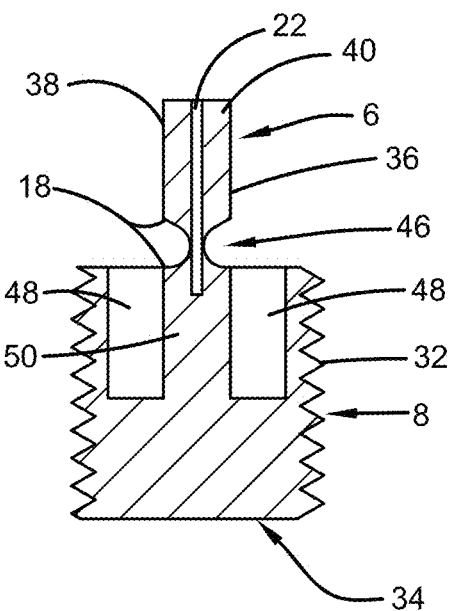
FIG. 5A  FIG. 5B
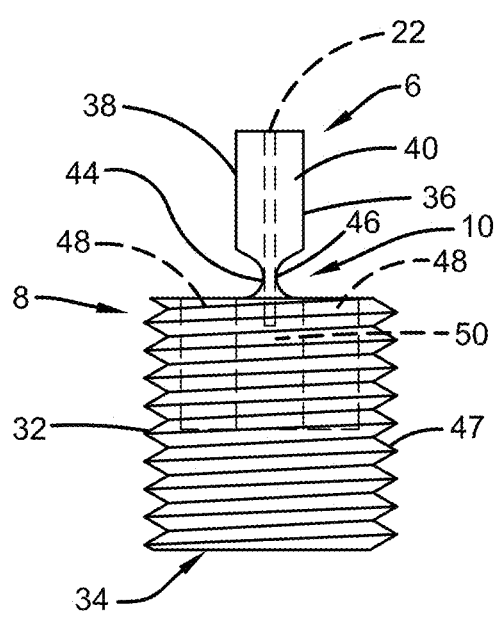
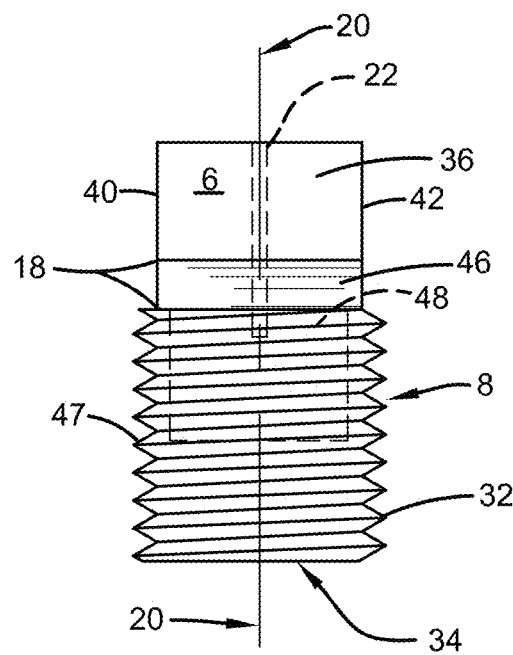
FIG. 5C  FIG. 5D

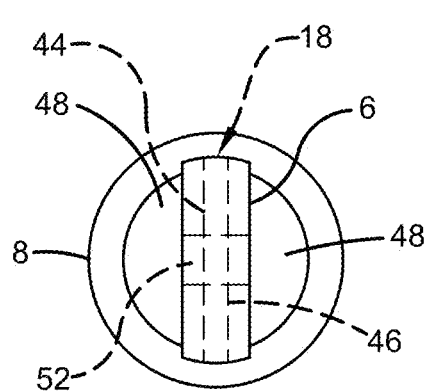 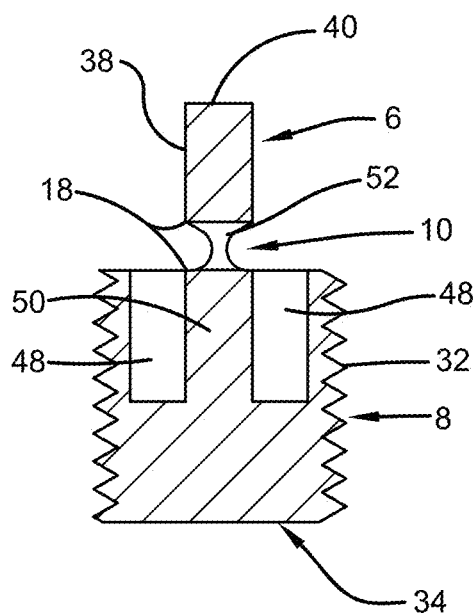
FIG. 6A       FIG. 6B
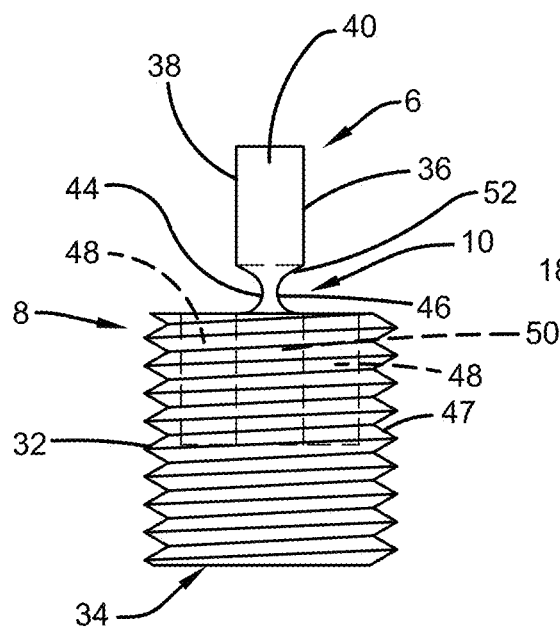 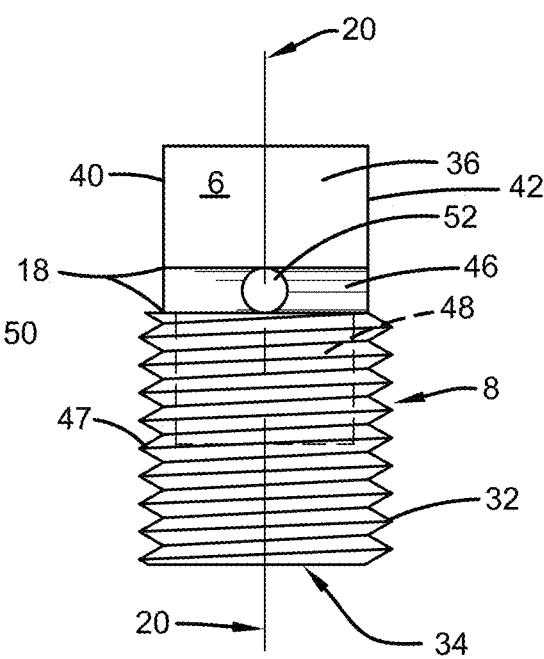
FIG. 6C       FIG. 6D

MINIMAL SHOCK SET SCREW

CROSS REFERENCE TO RELATED APPLICATIONS

This application claims the benefit of International Application No.: PCT/US2014/070309, entitled "Minimal Shock Set Screw," filed Dec. 15, 2014 which claims the benefit of U.S. provisional patent application Ser. No. 61/915,572 entitled "Minimal Shock Set Screw (MS3)," filed Dec. 13, 2013, both of which are incorporated herein by reference in their entirety.

FIELD OF THE INVENTION

The present invention relates to an improved breakaway set screw for use with surgical constructs for the spine having an improved geometry which reduces the shock to the patient and the surgeon during the set screw break off procedure.

BACKGROUND OF THE INVENTION

Spinal surgery using one or more surgical implants to stabilize, manipulate, and/or repair the spine is well known in the art. One type of common spinal surgery involves fusing or stabilizing two or more vertebra by application of a surgical construct to the posterior surfaces of the vertebra by means of pedicle screws.

There is a large market for pedicle screws and there are numerous designs and manufacturers of this type of fusion device. The spine market in the U.S. is $6.8 billion, and 34% of this market (over $2 billion) involves pedicle screw systems. These systems are usually placed bilaterally and the system on each side is typically composed of a minimum of one stabilizing rod, a pedicle screw for each vertebra, and a set screw at each pedicle screw to secure the stabilizing rod. Sometimes, the securing feature at the head of the pedicle screw is a separate connector. Each company has a slightly different design of the components, but generally, all pedicle screw constructs require a set screw to be tightened to a specific torque to ensure a proper connection between the pedicle screw and stabilizing rod, and thus a rigid fixation. It has been found that if the torque applied to the set screw is insufficient, the construct will lose integrity and the stabilizing rod will not be rigidly fixed as required and could slide or rotate. Additionally, an application of too much torque, it has been found, can result in a fracture of the vertebra or a loosening of the bone-implant connection. Too much torque can also severely deform the screw threads causing them to loose strength and to slip when the patient later puts a load on the spine or surgical construct.

Initially, a surgeon using these types of set screws would simply tighten them by hand until the surgeon judged that the proper tightness had been achieved. The problem with this approach was that there was no objective way for the surgeon to determine whether the set screw had been tightened to the required torque and the surgeon could easily apply too little or too much torque. And if there were a problem with the construct either during surgery or later, it was impossible for the surgeon to prove that the proper amount of torque had been applied.

To address these issues, a variety of systems were developed that utilized torque wrenches of various designs. These systems either required the surgeon to read the torque off the instrument during surgery or use a tightening tool that provides an audible sound and rotational slip when the proper torque had been reached. One problem with these prior art systems was the difficulty involved in reading the torque measurements or hearing and identifying the sound during surgery. In addition, the torque wrenches used in these systems could lose their precision with use and fail to undergo rotational slip at the target torque.

In another prior art system, the problems of the torque wrench based systems were avoided by means of breakaway set screws having a head designed to shear off the threaded body of the set screw once the proper torque has been achieved. While there are a variety of configurations known in the art, breakaway set screws are ordinarily made from a single piece of titanium alloy and have a hexagonal top portion that mates with a tightening device, a lower threaded set screw portion that mates with a threaded bore of a pedicle screw construct to secure a stabilizing rod, and an annular v-shaped notch separating the two portions.

In these prior art systems, the surgeon uses an extended counter torque tool that holds the top of the pedicle screw and stabilizing rod to try to limit or prevent transmission of the rotational torque used to tighten the set screw from being transmitted to the construct as a whole or to the vertebra of the patient. The shaft of the counter torque tool is hollow and sized to receive the shaft of a break off driver. The break off driver is longer than the counter torque tool and slides through the shaft of the counter torque tool to mate with the hexagonal head of the set screw. As set forth above, the hexagonal heads of these breakaway set screws are designed to shear off the threaded body of the set screw once the proper torque has been achieved. The surgeon simply turns the break off tool while keeping the counter torque tool still, until the hexagonal head shears off the threaded body of the set screw at the pre-determined torque. This set screw break off ("SSBO") procedure is repeated for all of the set screws in the construct. The SSBO procedure is performed 6 times for the average spinal implant construct and many more times for larger constructs in patients with severe deformities such as scoliosis.

Unfortunately, each SSBO imparts an immense, if short lived, shock to both the patient and the surgeon due to the energy released during the catastrophic failure of the metal at the V-shaped notch when the hexagonal head separates from the lower threaded set screw portion. Bench top studies of a prior set screw using accelerometers at various points on and around the pedicle screw have recorded a shock that averages between about 800 g and about 900 g, depending upon a variety of human factors, including how the tool was being held by the surgeon. (FIGS. 1A-B) This shock creates significant problems for both the patient and the surgeon. It can lead to the pedicle screw breaking through the side of the vertebra or fracturing the vertebra. The shock may also reduce the pull out strength of the pedicle screw in the patient, thus increasing the chance of a later revision surgery being required. These risks are particularly high for patients suffering with osteoporosis. Further, the repeated shock may also cause premature wear and/or injury to the surgeon's hands and significantly increases the chance that the tools could slip in the surgeon's hands causing pain or injury to the patient.

Accordingly, there is a need in the art for a breakoff set screw for use within a spinal surgery construct, wherein the shock to the patient and physician from the SSBO is significantly reduced.

SUMMARY OF THE INVENTION

In general, the present invention relates to an improved break off set screw for use with surgical constructs for the spine which reduce the shock to the patient and the surgeon during the set screw break off procedure.

In a first aspect, embodiments of the present invention are directed to a reduced shock breakaway screw comprising: an upper head portion having a top surface and configured to mate with a first torque applying device; a lower threaded screw portion configured to mate with a second torque applying device; a substantially annular groove separating the upper head portion from the lower threaded screw portion and defining a breakaway region; a central axis running from the top of the upper head portion to the bottom of the lower threaded screw portion; and a center hole running from the top of the upper head portion through the breakaway region and to or into the lower threaded screw portion; wherein the upper head portion will separate from the lower threaded screw portion upon application of a predetermined torque to the upper head portion.

In one or more embodiments, the breakaway region has an inner diameter defined by the diameter of the center hole and an outer diameter defined by a bottom of the substantially annular groove; and the inner diameter comprises from about 0.4% to about 90% of the outer diameter of the breakaway region. The reduced shock breakaway screw of claim 1 wherein: the breakaway region has an inner dimension defined by the area of the center hole and an outer dimension defined by the area circumscribed by a bottom of the substantially annular groove; and the area of the inner dimension comprises from about 0.0016% to about 81% of the area of the outer dimension of the breakaway region.

In one or more embodiments, the reduced shock breakaway screw may include any one or more of the above referenced embodiments of the first aspect of the present invention wherein the upper head portion has a non-circular cross sectional shape. In some embodiments the non-circular cross sectional shape may be square, rectangular, pentagonal, hexagonal, octagonal, Torx™, or triangular. In one or more embodiments, the reduced shock breakaway screw may include any one or more of the above referenced embodiments of the first aspect of the present invention wherein the lower threaded screw portion further comprises a nut portion configured to mate with the second torque applying device. In one or more embodiments, the reduced shock breakaway screw may include any one or more of the above referenced embodiments of the first aspect of the present invention wherein the nut portion has a non-circular cross sectional shape. In some embodiments, the non-circular cross sectional shape may be square, rectangular, pentagonal, hexagonal, octagonal, Torx™, and triangular.

In one or more embodiments, the reduced shock breakaway screw may include any one or more of the above referenced embodiments of the first aspect of the present invention wherein the lower threaded screw portion mates with the second torque applying device in such a way as to permit the second torque applying device to apply torque to the lower threaded screw portion without applying significant torque to the upper head portion. In one or more embodiments, the reduced shock breakaway screw may include any one or more of the above referenced embodiments of the first aspect of the present invention wherein the lower threaded screw portion further comprises one or more recessed openings configured to receive and mate with the second torque applying device.

In one or more embodiments, the reduced shock breakaway screw may include any one or more of the above referenced embodiments of the first aspect of the present invention wherein the lower threaded screw portion is configured to be received in a threaded bore of a surgical construct. In one or more embodiments, the reduced shock breakaway screw may include any one or more of the above referenced embodiments of the first aspect of the present invention wherein the lower threaded screw portion is configured to be received in a threaded bore located in a pedicle screw head, connector, ring, band clamp, or bone screw cap of a surgical construct for use with the spine of a patient. In one or more embodiments, the reduced shock breakaway screw may include any one or more of the above referenced embodiments of the first aspect of the present invention wherein the reduced shock breakaway screw is made from a titanium alloy, a stainless steel, or a cobalt-chromium alloy.

In a second aspect, embodiments of the present invention are directed to a reduced shock breakaway screw comprising: an upper head portion having a rectangular cross sectional area and configured to mate with a first torque applying device, wherein the upper head portion passes through a central axis of the reduced shock breakaway screw and has a first and second side, the distance between the first and second ends defining a length and the distance between the a first and second sides defining a width; a lower threaded screw portion connected to the upper head portion and having one or more recessed openings configured to mate with a second torque applying device; a first groove running along a bottom edge of the first side of the upper head portion; a second groove running along a bottom edge of the second side of the upper head portion; the first and second grooves defining a breakaway area; wherein the upper head portion will separate from the lower threaded screw portion upon application of a predetermined torque to the upper head portion.

In one or more embodiments, the reduced shock breakaway screw further comprises a first recessed opening in the lower threaded screw portion on a first side of the upper head portion and a second recessed opening in the lower threaded screw portion on a second side of the upper head portion. In one or more embodiments, the reduced shock breakaway screw may include any one or more of the above referenced embodiments of the second aspect of the present invention wherein the lower threaded screw portion engages the second torque applying device in such a way as to permit the second torque applying device to apply torque to the lower threaded screw portion without applying torque to the upper head portion.

In one or more embodiments, the reduced shock breakaway screw may include any one or more of the above referenced embodiments of the second aspect of the present invention further comprising a hole in the upper head portion running between the first and second grooves and passing through the central axis of the reduced shock breakaway screw. In one or more embodiments, the reduced shock breakaway screw may include any one or more of the above referenced embodiments of the second aspect of the present invention wherein the breakaway area has a substantially hour glass shape with its narrowest point at the central axis of the reduced shock breakaway screw. In one or more embodiments, the reduced shock breakaway screw may include any one or more of the above referenced embodiments of the second aspect of the present invention further comprising a hole in the upper head portion running between the first and second grooves and passing through the central axis of the reduced shock breakaway screw.

In one or more embodiments, the reduced shock breakaway screw may include any one or more of the above referenced embodiments of the second aspect of the present invention wherein the lower threaded screw portion is configured to be received in a threaded bore of a surgical construct for use with the one or more bones of a patient. In one or more embodiments, the reduced shock breakaway screw may include any one or more of the above referenced embodiments of the second aspect of the present invention wherein the reduced shock breakaway screw is made from a titanium or stainless steel.

BRIEF DESCRIPTION OF THE DRAWINGS

For a full understanding of the invention reference should be made to the following detailed description and the accompanying drawings, wherein:

FIG. 5A-D are a top plan view (FIG. 5A), a cross sectional view taken along the vertical plane (FIG. 5B), side elevational view (FIG. 5C), and front elevational view (FIG. 5D) of a reduced shock screw according to one or more embodiments of the present invention.

FIG. 6A-D are a top plan view (FIG. 6A), a cross sectional view taken along the vertical plane (FIG. 6B), side elevational view (FIG. 6C), and front elevational view (FIG. 6D) of a reduced shock screw according to one or more embodiments of the present invention.

DETAILED DESCRIPTION OF THE ILLUSTRATIVE EMBODIMENTS

Figure 1A:
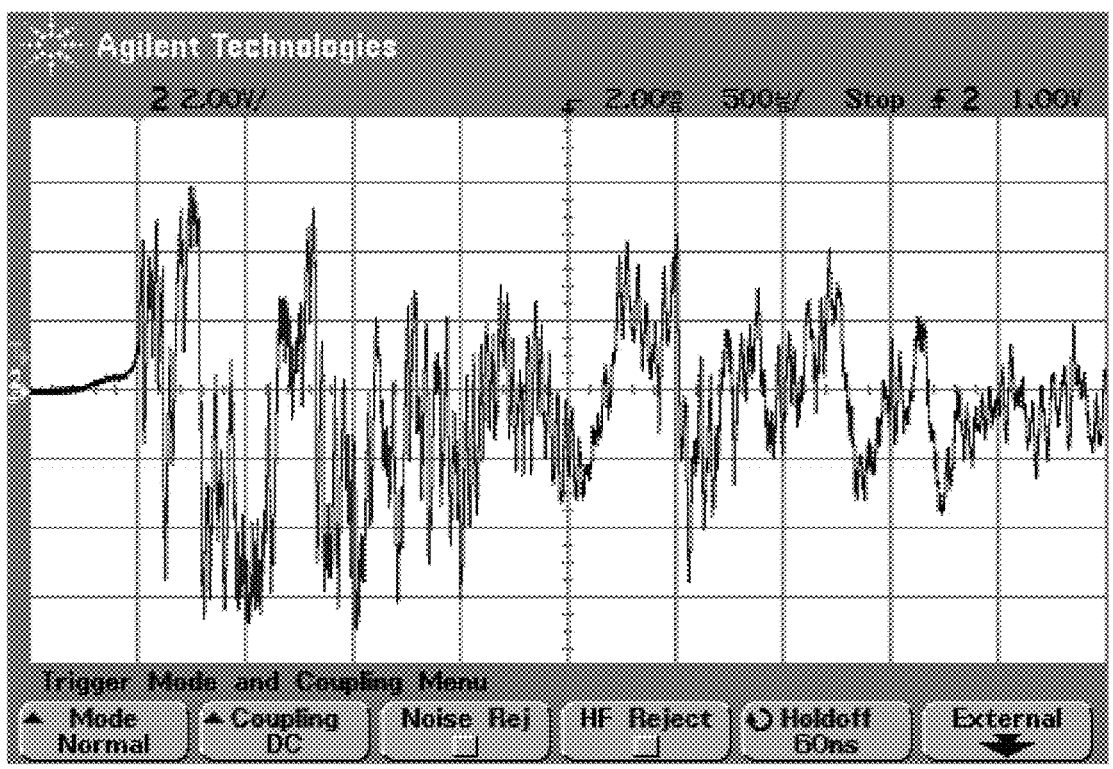
FIG. 1A is a printout of an oscilloscope output of the initial accelerometer signal recorded during SSBO of a commercially available prior art breakaway set screw.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

The present invention is generally directed to a reduced shock breakaway set screw for use with medical implants and the like having improved geometry of the cross-sectional area between the upper and lower portions of the set screw. The geometry serves to slow down the fracturing process during shearing, thereby increasing the proportion of energy dissipated as heat from plastic deformation of the material to the amount of energy released as kinetic energy from elastic rebound. The amount of energy released as shock to the patient or the surgeon is determined by the amount of energy released as kinetic energy of vibration as material elastically deformed and then snaps back to its previous condition.

Referring now to FIGS. 2-7, a reduced shock breakaway set screw is shown, generally indicated by the numeral 2. The reduced shock breakaway set screw 2 can be made of any ductile metal or other material that may be safely implanted in the human body and will not deform at or about the torque required for shearing. In one or more embodiments, the metal may be a titanium alloy, a stainless steel, or a cobalt-chromium alloy. In one embodiment the reduced shock breakaway set screw 2 is made of a commercially available Ti-6Al-4V Titanium alloy. In one embodiment the set screw 2 is made of a commercially available Ti 6Al-4V ELI Titanium alloy. In one embodiment the reduced shock breakaway set screw 2 is made of a commercially available 316L stainless steel. In one embodiment, the reduced shock breakaway set screw 2 may be machined out of a solid piece of a titanium alloy, stainless steel or cobalt-chromium alloy. In accordance with at least one aspect of the present invention, the reduced shock set screw may undergo any of the conventional or otherwise appropriate surface treatments.

In some embodiments, the reduced shock breakaway screw 2 may be adapted to be used in securing a spinal rod or other elongated member within a pedicle screw head, connector, ring, band clamp, bone screw cap, or other portion of a surgical construct in such a way as to substantially eliminate translational or rotational movement of the rod with respect to the vertebra or other parts of the surgical construct. As used herein, a surgical construct for use with the spine is a multicomponent device constructed from stainless steel or a titanium alloy, consisting of solid, grooved, or slotted plates or rods (usually using metal or PEEK) that are longitudinally interconnected and anchored to adjacent vertebrae using bolts, hooks, or screws. In some embodiments, the reduced shock breakaway screw 2 may be a set screw. In some embodiments, the reduced shock breakaway screw 2 may be used in other orthopedic applications where a reduced shock breakaway screw may be required.

The reduced shock breakaway screw 2 has an outer surface 4 and can be divided into an upper head portion 6 and a lower threaded screw portion 8, separated by a substantially annular groove 10. Substantially annular groove 10 is best shown in FIG. 2E and has an upper wall 12, a lower wall 14 and a bottom 16. The area circumscribed by substantially annular groove 10 defines a break-away region 18 (see FIG. 2C), where upper head portion 6 separates from lower threaded set screw portion 8 during the break off process. The size and shape of substantially annular groove 10 are not particularly limited except to the extent that they affect the torque at which break off occurs. As will be appreciated by those known in the art, the break off torque value may be affected by the material used for the screw and the depth and shape of the groove. One of ordinary skill in the art will be able to optimize these variables to obtain a desired break off torque. In embodiments such as those shown in FIGS. 2-4, lower wall 14 is approximately perpendicular to a central axis 20 running the length of reduced shock breakaway screw 2. In some embodiments, the volume of the breakaway area 18 is from 10% to 95% of that area of the screw prior to formation of the substantially annular groove 10. In some embodiments, the volume of the breakaway area 18 is from 50% to 95% of that area of the screw prior to formation of the substantially annular groove 10.

In some embodiments, the machine lathe insert used to machine the substantially annular groove 10 has a nose radius of from sharp to 1/16 inch. In some embodiments, the machine lathe insert used to machine the substantially annular groove 10 has a nose radius of from 1/500 inch to 3/64 inch. In some embodiments, the machine lathe insert used to machine the substantially annular groove 10 has a nose radius of from 1/200 inch to 1/32 inch. In some embodiments, the radius of groove bottom 16 is 0.0156 inches.

Figure 2A:
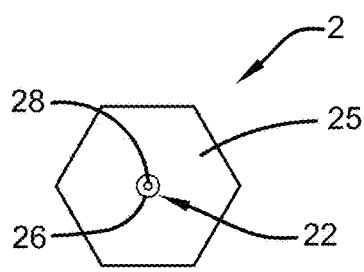
FIGS. 2A-E are a top plan view (FIG. 2A), front elevational view (FIG. 2B), a cross sectional view taken along the plane indication in FIG. 2B (FIG. 2C), a cross sectional view taken along the vertical plane (FIG. 2D), and an enlarged cutout from FIG. 2D showing the substantially annular groove (FIG. 2E) of a reduced shock screw according to one or more embodiments of the present invention.
Figure 2C:
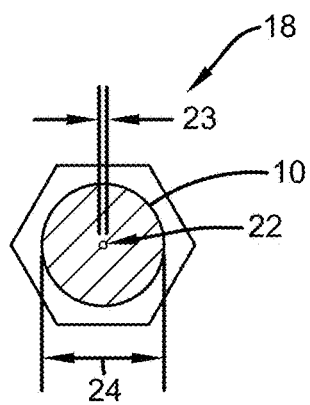
Figure 2B:
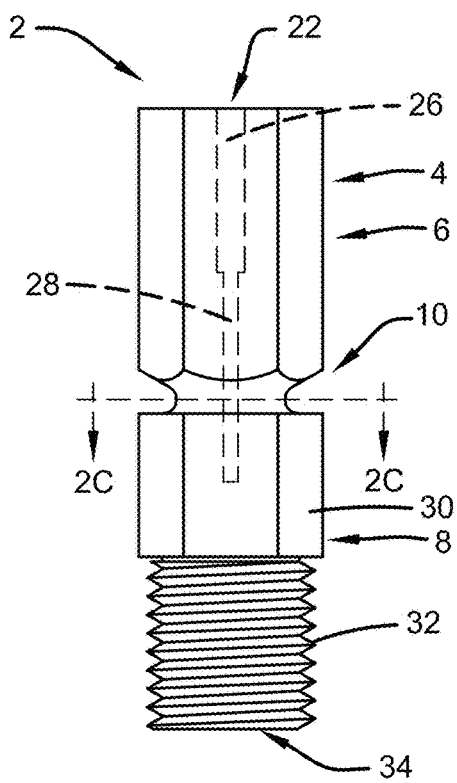
Figure 2D:
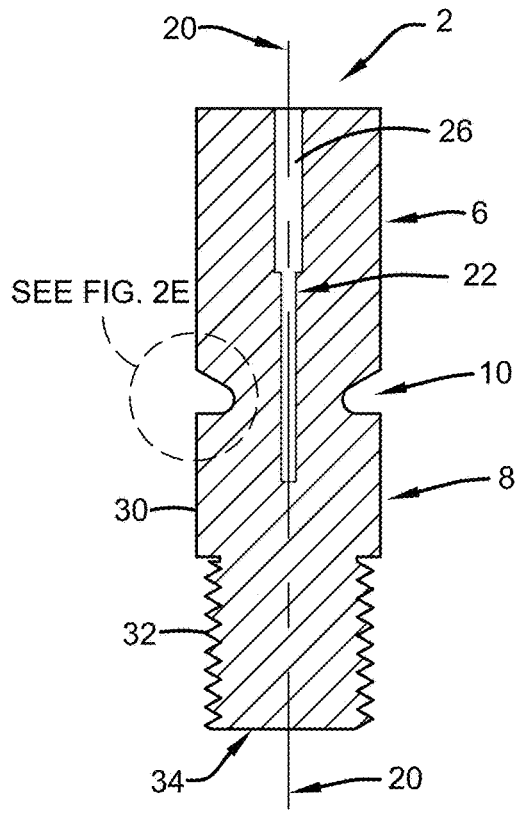
Figure 2E:
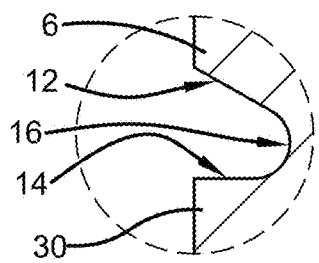
Figure 3A:
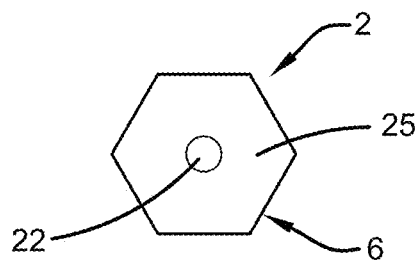
FIG. 3A-C are a top plan view (FIG. 3A), front elevational view (FIG. 3B), and a cross sectional view taken along the vertical plane (FIG. 3C) of a reduced shock screw according to one or more embodiments of the present invention.
Figure 3B:
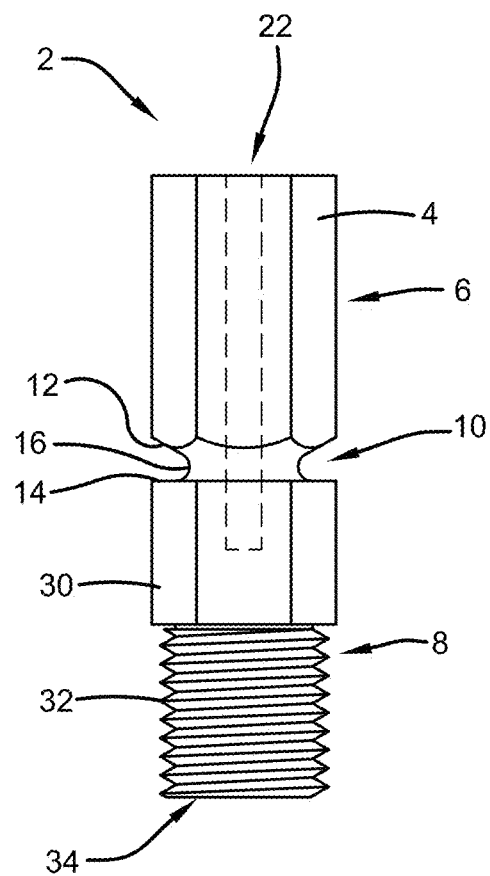
Figure 3C:
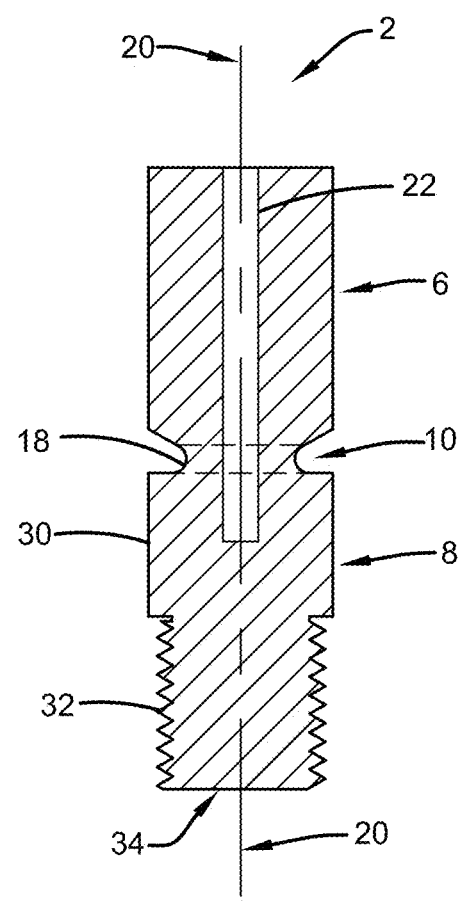

In the embodiments shown in FIGS. 2 and 3, reduced shock breakaway screw 2 may have a center hole 22 running from the top surface 25 of the upper head portion 6, through upper head portion 6 generally along a central axis 20 and to or into lower threaded set screw portion 8. While not being bound to a particular theory, it is believed that center hole 22, helps to limit or prevent variation from the calculated break-off torque by ensuring that the center of rotation of rectangular breakaway region 18 stays centered and the center of torsional failure/rotation to be constricted to intended area.

As those of ordinary skill in the art will appreciate, there can be significant problems machining a long narrow hole like center hole 22. In the embodiment shown in FIG. 2, center hole 22 may comprise a first hole portion 26 having a wider diameter and a second hole portion 28 having a narrower diameter. As will be discussed further below, the diameter of the second hole portion 28 where it passes through the break-away region 18 may have a significant impact on break off mechanics of the reduced shock breakaway screw the present invention. The diameter of the first hole portion 26, however, does not significantly affect the break off mechanics provided that it is not so large as to compromise the integrity of the upper head portion 6. First hole portion 26 is intended to make it easier to drill the second hole portion 28. As will be appreciated by those of skill in the art, the small diameter drill bits used to machine center hole 22 in some embodiments cannot withstand as much resistance as larger diameter drill bits. The walls of first hole portion 26 do not contact and therefore do not to impart any resistance upon the small bit of drilling second hole portion 28. In some embodiments, first hole portion 26 may have any diameter more than 0.002 inches. This reduces the total resistance felt by the bit, and thus the likelihood that the small drill-bit will break.

In some embodiments, second hole portion 28 may have a diameter of from about 0.001 inches to about 0.227 inches. In some embodiments, second hole portion 28 may have a diameter of from about 0.013 inches to about 0.125 inches. In some embodiments, second hole portion 28 may have a diameter of from about 0.01 inches to about 0.05 inches. In some embodiments, second hole portion 28 may have a diameter of about 0.013 inches. In some embodiments, second hole portion 28 may have a diameter of about 0.030 inches.

In the embodiment shown in FIG. 3, center hole 22 has the same diameter throughout its length. In some of these embodiments, a larger drill bit may be used to avoid some of the problems with use of a smaller drill bit discussed above. In some embodiments, center hole 22 may have a diameter of from about 0.001 inches to about 0.227 inches. In some embodiments, center hole 22 may have a diameter of from about 0.013 inches to about 0.125 inches. In some embodiments, center hole 22 may have a diameter of from about 0.01 inches to about 0.05 inches. In some embodiments, center hole 22 may have a diameter of about 0.013 inches. In some embodiments, center hole 22 may have a diameter of about 0.030 inches.

FIG. 2C shows a cross section of the reduced shock breakaway set screw 2 at breakaway region 18. As can be seen from FIG. 2C, center hole 22 defines an inner diameter 23 of breakaway region 18 and the diameter of the reduced shock breakaway set screw 2 measured at the bottom 16 of substantially annular groove 18 defines an outer diameter 24 of breakaway region 18. It is envisioned that the inner diameter 23 of breakaway region 18 (center hole 22) be relatively small in comparison to the outer diameter 24 of the breakaway region 18 (diameter of the reduced shock breakaway set screw 2 at the bottom 16 of substantially annular groove 18). In some embodiments like that shown in FIG. 2C, breakaway region 18 may be substantially circular and the ratio of the inner diameter 23 to the outer diameter 24 of the breakaway region 18 expressed as a percent may be from about 0.4% to about 90%. In some embodiments, breakaway region 18 is substantially circular and the ratio of the inner diameter 23 to the outer diameter 25 of the breakaway region 18 expressed as a percent may be from about 2% to about 30%. In some embodiments, breakaway region 18 is substantially circular and the ratio of the inner diameter 23 to the outer diameter 24 of the breakaway region 18 expressed as a percent may be from about 5% to about 25%. In some embodiments, breakaway region 18 is substantially circular and the ratio of the inner diameter 23 to the outer diameter 24 of the breakaway region 18 expressed as a percent may be about 7.7%. In some embodiments, breakaway region 18 is substantially circular and the ratio of the inner diameter 23 to the outer diameter 24 of the breakaway region 18 expressed as a percent may be about 17.7%.

In some other embodiments, the cross sectional shape of the breakaway region 18 is not round and it is more accurate to compare the area of center hole 22 to the area circumscribed by the bottom 16 of substantially annular groove 10 and the ratio may be expressed in terms of a percent. In some embodiments, the cross-sectional area (diameter) of center hole 22 may be from about 0.0016% to about 81% of the cross sectional area of the reduced shock breakaway set screw 2 measured at the bottom 16 of substantially annular groove 10. In some embodiments, the cross-sectional area (diameter) of center hole 22 may be from about 0.0016% to about 25% of the cross sectional area of the reduced shock breakaway set screw 2 measured at the bottom 16 of substantially annular groove 10.

Upper head portion 6 is configured to mate with a first torque applying tool (not shown). In embodiments where first torque applying tool mates with its outer surface(s), upper head portion 6 may have any non-circular cross sectional shape. As can be seen in FIGS. 2-3, upper head portion 6 may be hexagonal in cross section for some or all of its length and sized to fit within and mate with a drive socket of a socket wrench or torque wrench, a manual torqueing instrument, or other torque generating tool having a hollow end portion that is hexagonal in cross section and intimately fits over the upper head portion 6. As will be appreciated by those of skill in the art, however, upper head portion 6 may have any non-circular cross sectional shape so long as it mates with the first torque applying tool in such a way as to permit the torque applying tool to apply an amount of torque sufficient to cause the upper head portion 6 to shear off of the threaded lower set screw portion 8. In embodiments such as the one shown in FIG. 4, upper head portion 6 may have a Torx™ cross-section for some or all of its length and sized to fit within and mate with a drive socket of a socket wrench or torque wrench, a manual torqueing instrument, or other torque generating tool having a hollow end portion with a Torx™ cross section and intimately fits over the upper head portion 6. In some embodiments, upper head portion 6 may have a cross sectional shape that is, without limitation, square, rectangular, pentagonal, hexagonal, octagonal, Torx™, and triangular.

In some embodiments, the top surface 25 of upper head portion 6 may also have a recess (not shown) that is shaped to receive within it the end portion of a torque applying tool or a drive bit, so long as the arrangement permits the torque applying tool to apply the necessary amount of torque to cause the upper head portion 6 to shear off of the threaded lower set screw portion 8. In some of these embodiments, the upper head portion 6 may also be circular since it need not be gripped at its outer surface.

Figure 4A:
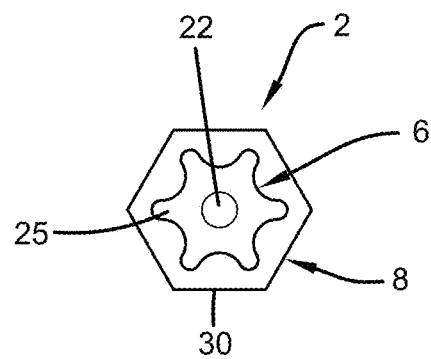
FIG. 4A-C are a top plan view (FIG. 4A), front elevational view (FIG. 4B), and a cross sectional view taken along the vertical plane (FIG. 4C) of a reduced shock screw according to one or more embodiments of the present invention.
Figure 4B:
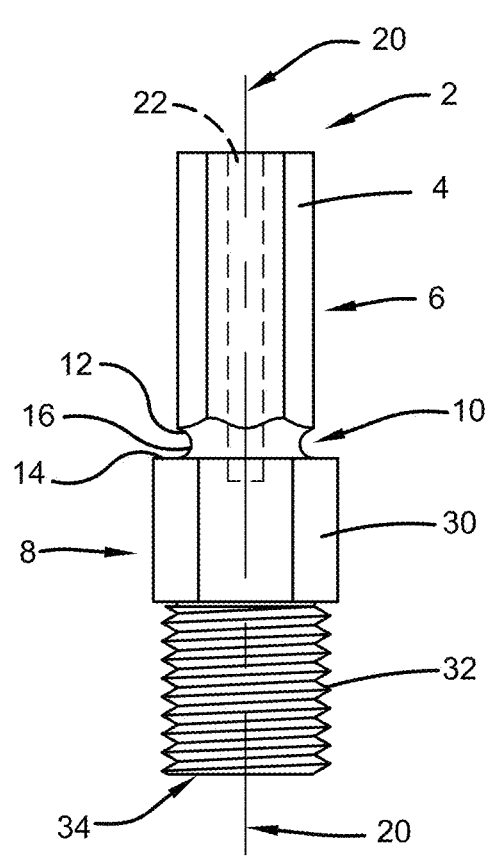
Figure 4C:
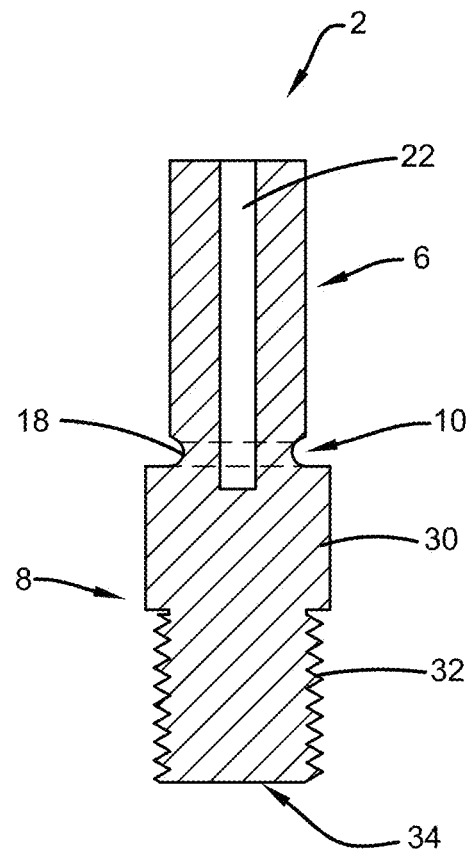
Figure 7A:
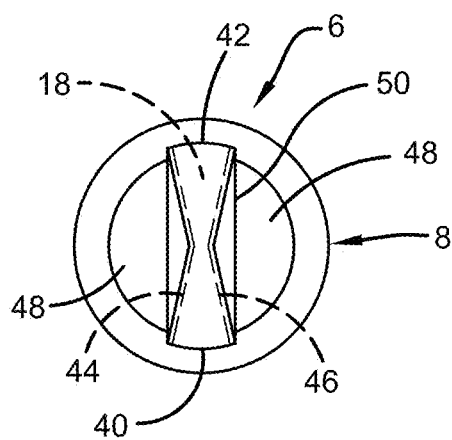
FIG. 7A-B are a top plan view (FIG. 7A) and a front elevational view (FIG. 7B) of a reduced shock screw according to one or more embodiments of the present invention comprising a breakaway region having an hourglass cross sectional shape.
Figure 7C:
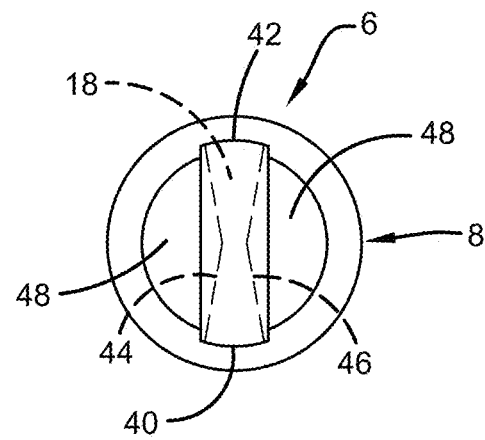
FIG. 7C-D are a top plan view (FIG. 7C) and a cross sectional view taken along the vertical plane (FIG. 7D) of a reduced shock screw according to one or more embodiments of the present invention comprising a breakaway region and upper head portion having an hourglass cross sectional shape.
Figure 7B:
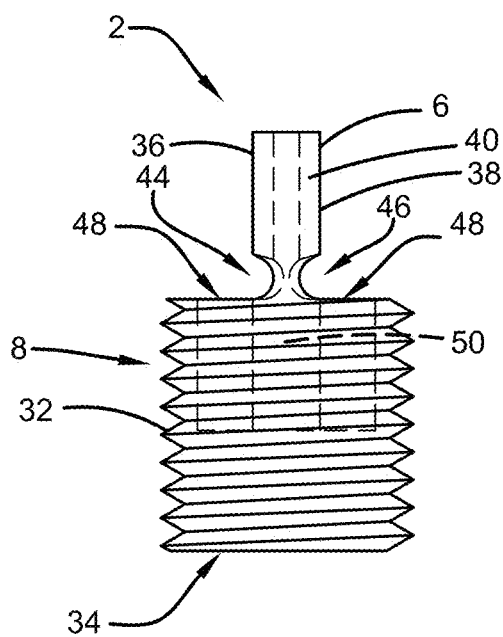
Figure 7D:
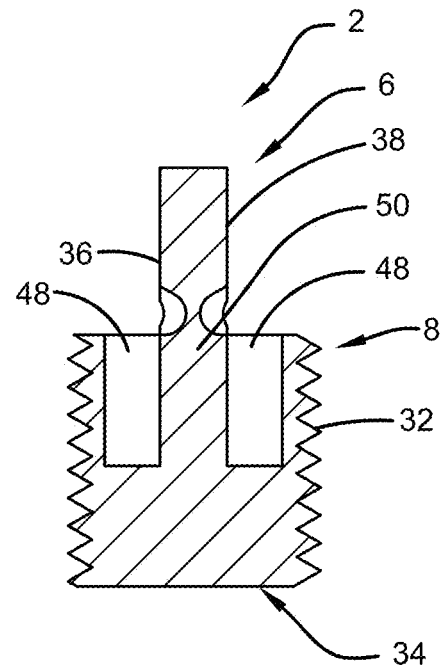

The threaded lower set screw portion 8 is shown in FIGS. 2-4 and comprises a nut portion 30, a threaded portion 32 sized to fit in a threaded bore located in a pedicle screw head, connector, ring, band clamp, bone screw cap, or other similar portion of a surgical construct for use with the spine, to anchor a rod or other elongated member to a pedicle screw, and a set screw end portion 34. In these embodiments, nut portion 30 is located immediately below substantially annular groove 10 and may have any non-circular cross sectional shape including, without limitation, square, rectangular, pentagonal, hexagonal, octagonal, Torx™, and triangular that is configured to mate with a second torque applying tool (not shown).

In the embodiments shown in FIGS. 2 and 3, nut portion 30 has a hexagonal cross section and is sized to fit within and mate with a drive socket of a socket wrench or torque wrench, a manual torqueing instrument, or other torque generating tool having a hollow end portion that is hexagonal in cross section and intimately fits over the nut portion 30. As also shown in FIGS. 2 and 3, nut portion 30 and upper head portion 6 may have the same cross section, but this need not be the case as can be seen from FIG. 4, where nut portion 30 of threaded lower set screw portion 8 has a hexagonal cross section and the upper head portion 6 has a Torx™ cross section. Like upper head portion 6, nut portion 30 of threaded lower set screw portion 8 may have any cross sectional shape so long as can mate with a second torque applying tool while upper head portion 6 is still attached to the reduced shock breakaway set screw 2.

That being said, it should be apparent to those of ordinary skill in the art that in the embodiments shown in FIGS. 2-4, threaded lower set screw portion 8 will ordinarily remain inside the patient as part of the surgical construct being created. And since the nut portion 30 of threaded lower set screw portion 8 does not fit in the threaded bore of a pedicle screw head, connector, ring, band clamp, bone screw cap, or other similar portion of a surgical construct as does the threaded portion 32, nut portion 30 of the reduced shock breakaway set screw 2 will protrude out from the top of the threaded bores of the surgical constructs in which is being used. Accordingly, it is envisioned that the height of the nut portion 30 as measured from the top of the threaded portion 32 to the lower wall 14 of the substantially annular groove 10 be minimized to the extent possible, so long as it can still mate with a second torque applying tool while upper head portion 6 is still attached to the reduced shock breakaway set screw 2 in such a way as to function as described herein.

It is envisioned that a second torque applying tool (not shown) be configured to mate with the nut portion 30 in such a way that it may be used to tighten and/or loosen the reduced shock breakaway set screw 2 prior to break off without applying significant torque to upper head portion 6. As used herein, the term "significant torque" refers to more than a de minimus amount of torque and includes any amount of torque capable of fatiguing and/or weakening the metal in the break-away region 18. In this manner, nut portion 30 permits the reduced shock breakaway set screw 2 to be tightened or loosened prior to break off without fatiguing and/or weakening the metal in the break-away region 18, thereby reducing the chances that the upper head portion 6 will break off before the required torque has been achieved. This also allows the user to partially (but not fully) tighten and loosen the reduced shock breakaway screws 2 as necessary to position and/or reposition various parts of the construct being used to achieve the desired configuration, provided the torque applied in doing so does not reach the break off torque for the screw 2. As will be apparent to those of skill in the art, while tightening the screw using nut portion 30 avoids fatiguing and/or weakening the metal in the break-away region 18, there is nothing to prevent the very overtightening that the breakaway screw was designed to prevent. Accordingly, great care must be taken when partially tightening reduced shock breakaway screws 2 using nut portion 30.

Once the desired configuration has been achieved, the first torque applying tool (not shown) which, as described above, is configured to mate with upper head portion 6 without engaging nut portion 30 may be used to finish tightening the reduced shock breakaway set screws 2. Since the torque is applied to upper head portion 6 and not nut portion 30 of threaded lower set screw portion 8, the torque being applied is brought to bear on the metal in break-away region 18 of the reduced shock breakaway set screw 2 causing upper head portion 6 to sheer off of threaded set screw portion 8. Since the break-away region 18 of the reduced shock breakaway set screw 2 is designed to break at specific desired torque, tightening the screws until break off ensures that the proper torque has been applied. In addition, after upper head portion 6 has been broken off of threaded set screw portion 8, it is envisioned that the second torque applying tool also may be used to loosen or remove threaded set screw portion 8.

As set forth above, threaded portion 32 may be sized to fit in a threaded bore located in a pedicle screw head, connector, ring, band clamp, bone screw cap, or other similar portion of a surgical construct for use with the spine, to anchor a rod or other elongated member to a pedicle screw. When reduced shock breakaway set screw 2 is tightened as described above, the set screw end portion 34 of comes into engagement with the rod or other elongated member, holding it in place. The set screw end 34 can be any shape or configuration that can securely hold the rod or other elongated member in place and prevent either translational or rotational movement of the rod or other elongated member. Possible configurations for set screw end 34 may include, without limitation, a v-shaped point coaxial with the lower screw portion 8, sharpened ring with or without a v-shaped point coaxial with the lower screw portion 8, or any other conventional or otherwise suitable configuration.

Turning now to the embodiments shown in FIGS. 5 and 6. In these embodiments, upper head portion 6 has a substantially rectangular cross section and runs across the top of threaded set screw portion 8 and passes through the central axis 20 of the reduced shock breakaway screw 2. In these embodiments, upper head portion 6 may have a first and a second side portion 36, 38 and a first and second end portion 40, 42, the distance between the first and second end portion 40, 42, defining a length of upper head portion 6, and the distance between the first and a second side portions 36, 38, defining the width of upper head portion 6. In some embodiments, the length of the upper head portion 6 may be substantially equal to the diameter of threaded screw portion 8. In some embodiments, the length of the upper head portion 6 may be less than the diameter of threaded set screw portion 8.

In some of these embodiments, substantially annular groove 10 runs around the bottom edge of upper head portion 6, just above threaded screw portion 8 and defines breakaway region 18. In the embodiments shown in FIGS. 5 and 6, however, substantially annular groove 10 does not run the entire way around the bottom edge of upper head portion 6. Instead, substantially annular groove 10 comprises a first and a second groove 44, 46 running along the bottom edge of the first and second sides 36, 38, respectively and there are no grooves in the first and second ends 40, 42. In these embodiments, breakaway region 18 may be defined as the area between the first groove 44 and the second groove 46.

As with the embodiments of FIGS. 2-4, the substantially annular groove 10 in the embodiments shown in FIGS. 5-7, has an upper wall 12, a lower wall 14 and a bottom 16 as shown in FIG. 2E. As it is preferred to minimize the amount of material left above the lower threaded portion 8 after break off, there is generally little or no space left between the threads 47 of lower threaded portion 8 and the lower wall 14 of the substantially annular groove 10. In these embodiments, the lower wall 14 of substantially annular groove 10 will generally be oriented perpendicular to central axis 20. The angle of the upper wall 12 relative to lower wall 14 in one or more of the embodiments shown FIGS. 5-7 will depending upon the particular tool used to machine substantially annular groove 10. In some embodiments, the angle between the upper wall 12 relative and lower wall 14 may be between 5 degrees and 90 degrees. In some embodiments, the angle between the upper wall 12 relative and lower wall 14 may be between 15 degrees and 70 degrees. In some embodiments, the angle between the upper wall 12 relative and lower wall 14 may be between 15 degrees and 60 degrees. In some embodiments, the angle between the upper wall 12 relative and lower wall 14 may be 60 degrees.

As described above, the size and shape of substantially annular groove 10 are not particularly limited except to the extent that they affect the torque at which break off occurs. As will be appreciated by those known in the art, the break off torque value may be affected by the material used for the screw and the depth and shape of the groove. One of ordinary skill in the art will be able to optimize these variables to obtain a desired break off torque. In some embodiments, the volume of the breakaway area 18 is from 10% to 95% of that area of the screw prior to formation of the substantially annular groove 10. In some embodiments, the volume of the breakaway area 18 is from 50% to 95% of that area of the screw prior to formation of the substantially annular groove 10.

In some embodiments, the machine lathe insert used to machine the substantially annular groove 10 has a nose radius of from sharp to $1/16$ inch. In some embodiments, the machine lathe insert used to machine the substantially annular groove 10 has a nose radius of from $1/500$ inch to $3/64$ inch. In some embodiments, the machine lathe insert used to machine the substantially annular groove 10 has a nose radius of from $1/200$ inch to $1/32$ inch. In some embodiments, the radius of groove bottom 16 is 0.0156 inches.

In embodiments such as those shown in FIGS. 5-7, lower wall 14 is approximately perpendicular to a central axis 20 running the length of reduced shock breakaway screw 2.

Further, as can be seen in FIGS. 5 and 6, threaded set screw portion 8 does not have a nut portion 30. Instead, threaded set screw portion 8 comprises one or more recessed openings 48 configured to receive a second torque applying tool (not shown). The one or more recessed openings 48 may have any cross sectional shape provided that they are configured to mate with the second torque applying tool and are not so large as to affect the structural integrity of the reduced shock breakaway set screw 2. In some embodiments, recessed openings 48 may have a circular sector cross section. In some embodiments, recessed openings 48 may have a semicircular cross section. In some embodiments, recessed openings 48 may have a rectangular cross section. In some embodiments, recessed openings 48 may have a square cross section.

As shown in FIGS. 5-7, recessed openings 48 may be located one either side of upper head portion 6, and the second torque applying tool is therefore configured to go over upper head portion 6 and mate with recessed openings 48 on either side of upper head portion 6. In the embodiments shown in FIGS. 5-7, the area between recessed openings 48 defines a post 50 spanning the diameter of the threaded set screw portion 8 immediately below breakaway region 18. Post 50 may have any cross sectional shape, including but not limited to the same cross sectional area as the upper head portion 6. In some embodiments, post 50 may have a rectangular cross sectional shape. In some embodiments, post 50 may have a hourglass shaped cross sectional shape. Recessed openings 48 may be located anywhere in threaded set screw portion 8 provided that such locations permit use of the second torque applying tool while upper head portion 6 is still attached to the reduced shock breakaway set screw 2 and permit the second torque applying tool to apply torque evenly throughout the rotation of screw 2.

As set forth above, torque may be applied to the threaded set screw portion 8 by inserting the second torque applying tool (not shown) into one or more recessed openings 48 in threaded set screw portion 8. This arrangement permits the reduced shock breakaway set screw 2 to be tightened or loosened prior to break off without fatiguing and/or weakening the metal in the break-away region 18 of the reduced shock breakaway set screw 2, thereby reducing the chances that the upper head portion 6 will break off before the required torque has been achieved. This also allows the user to partially (but not fully) tighten and loosen the reduced shock breakaway set screws 2 as necessary to position and/or reposition various parts of the construct being used to achieve the desired configuration, provided the torque applied in doing so does not reach the break off torque for the screw 2.

And as set forth above, once the desired configuration has been achieved, the first torque applying tool (not shown) which, as described above, is configured to mate with upper head portion 6 without engaging recessed openings 48 may be used to finish tightening the reduced shock breakaway set screws 2. Since the torque is applied to upper head portion 6 and not threaded lower set screw portion 8, the torque being applied is brought to bear on the metal in breakaway region 18 causing upper head portion 6 to sheer off of threaded set screw portion 8. Since the break-away region 18 of the reduced shock breakaway set screw 2 is designed to break at specific desired torque, tightening the screws until break off ensures that the proper torque has been applied. In addition, after upper head portion 6 has been broken off of threaded set screw portion 8, it is envisioned that the second torque applying tool (not shown) also may be used to loosen or remove threaded set screw portion 8.

As can be seen in the embodiment shown in FIG. 6, a transverse hole 52 may be provided through break-away region 18 of substantially annular groove 10 and through central axis 20. In some embodiments, transverse hole 52 may have a diameter of from about 1% to about 100% of the height of the substantially annular groove 10. In some embodiments, transverse hole 52 may have a diameter of from about 5% to about 90% of the height of the substantially annular groove 10. In some embodiments, transverse hole 52 may have a diameter of from about 20% to about 80% of the height of the substantially annular groove 10. In some embodiments, transverse hole 52 may have a diameter of from about 40% to about 60% of the height of the substantially annular groove 10. While not being bound to a particular theory, it is believed that transverse hole 52, helps to limit or prevent variation from the calculated break-off torque by ensuring that the center of rotation of rectangular breakaway region 18 stays centered and the the center of torsional failure/rotation to be constricted to intended area.

The embodiment shown in FIG. 7 is substantially similar to the embodiments shown in FIGS. 5 and 6, except that rather than having a rectangular cross sectional shape, breakaway region 18 has a substantially hour glass shaped cross sectional shape. In some embodiments, substantially hour glass shaped breakaway region 18 may be formed by using an upper head portion 6 that has a generally hour glass shaped cross sectional shape. (See FIGS. 7A, 7B) In some other embodiments, substantially hour glass shaped breakaway region 18 may be formed by gradually increasing the depth of substantially annular groove 10 (and/or first and second grooves 44, 46) as it goes from the outer edge of the screw to the center and then reversing the process moving from the center back out to the outer edge screw for the substantially annular groove 10 (and/or first and second grooves 44, 46) on both sides of upper head portion 6. (See FIGS. 7C, 7D) In both of these embodiments, the central axis passes through the narrowest point of the hourglass shaped cross section of the breakaway region 18. See FIGS. 7A, 7C.

It should also be appreciated that depending upon the type of tool used to cut them, changes in the depth of the substantially annular groove 10 (and/or first and second grooves 44, 46) may also affect its height. Where the tool used makes a groove having a flat bottom wall and an angled upper wall as is shown in FIG. 2E, then the deeper the tool goes into the metal, the wider the groove will be. Where, as in FIGS. 2-6 and 7A, the substantially annular groove 10 (and/or first and second grooves 44, 46) has a uniform depth, the groove height will likewise be uniform. However, in embodiments where the depth of the substantially annular groove 10 (and/or first and second grooves 44, 46) varies as it does in FIG. 7B, the height of the groove will increase as function of its depth.

While not to be bound to theory, it is believed that, like transverse hole 52 described above, the hourglass shaped breakaway region 18 helps to limit or prevent variation from the calculated break-off torque by ensuring that the center of rotation of rectangular breakaway region 18 stays centered and the center of torsional failure/rotation to be constricted to intended area.

In some embodiments, hourglass shaped upper head portion 6 may further comprise a transverse hole (not shown) through break-away region 18 of substantially annular groove 10 (and/or first and second grooves 44, 46) and through central axis 20. As set forth above, in some embodiments transverse hole 52 may have a diameter of from about 1% to about 100% of the height of the substantially annular groove 10. In some embodiments, transverse hole 52 may have a diameter of from about 5% to about 90% of the height of the substantially annular groove 10. In some embodiments, transverse hole 52 may have a diameter of from about 20% to about 80% of the height of the substantially annular groove 10. In some embodiments, transverse hole 52 may have a diameter of from about 40% to about 60% of the height of the substantially annular groove 10.

The one or more embodiment of the present invention as shown in FIGS. 5-7, reduced shock breakaway set screw 2 may also have a center hole 22 running from the top of upper head portion 6 along the central axis 20 and to or into the lower threaded screw portion 8, as described above. (See FIG. 5)

Figure 8:
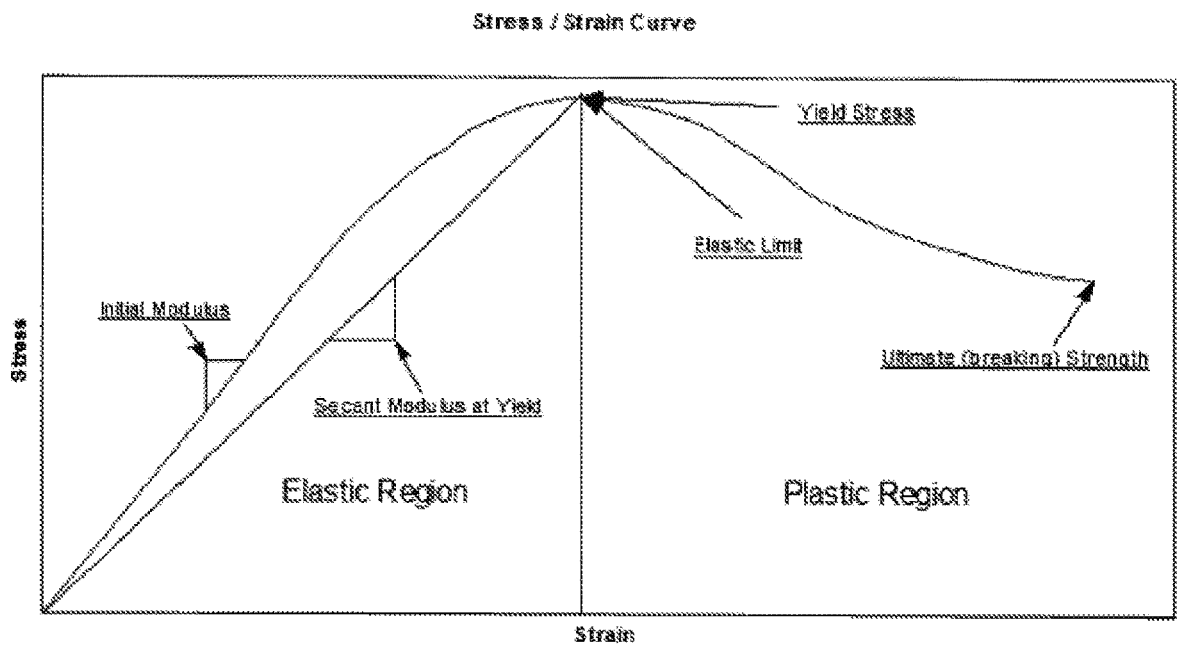
FIG. 8 is a generic stress strain curve showing the elastic and plastic deformation regions.
Figure 9:
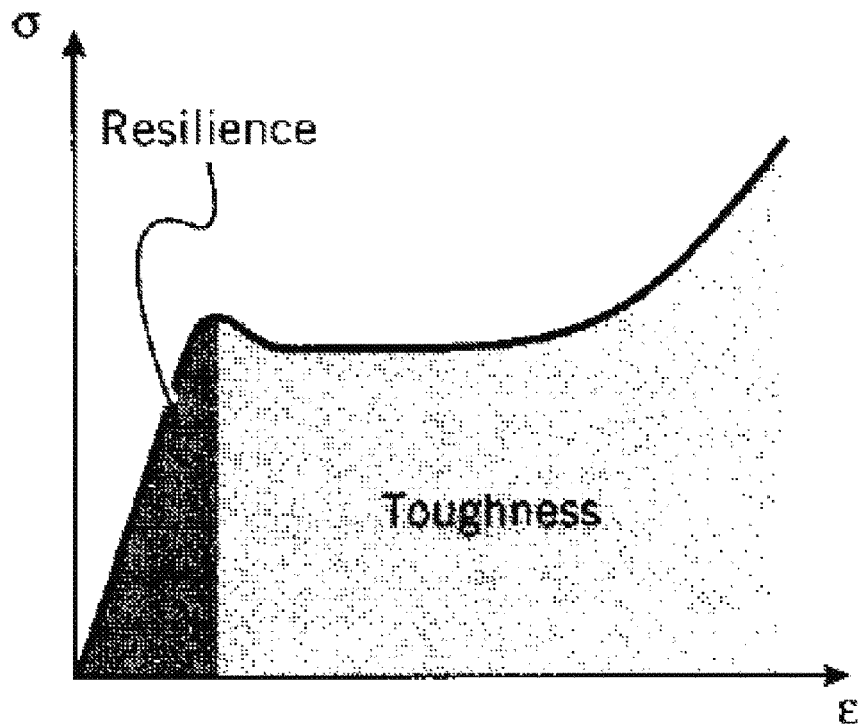
FIG. 9 is a stress strain curve wherein area under the curve is the indicative of a material's toughness.

The external work performed on the device by applying torque to the reduced shock breakaway set screw 2 is primarily converted into either plastic dissipation energy or recoverable elastic strain energy that manifests itself as shock. FIG. 8 is a generic stress strain curve showing areas of elastic and plastic deformation. Plastic deformation for most materials is caused when the structure undergoes so much stress that the bonds between individual atoms break and reform to an adjacent atom. Plastic deformation happens in the direction that these atoms move. Essentially, this concept relies on the material's toughness, or energy absorption potential before failure. Visually, one can see a material's toughness by observing the area under the engineering stress-strain curve (See FIG. 9). When a metal is elastically deformed, there is no such breaking and reforming of bonds within the metal and if the material breaks/shears under only elastic deformation, the material sections will snap back to the original shape releasing essentially all of the elastic strain energy as kinetic energy in the form of vibrations (i.e. shock).

Therefore, it is believed that as the elastic strain energy decreases relative to plastic dissipation energy, the shock will also decrease. As would be clear to one of ordinary skill in the art from simple geometry, as the upper head portion of the breakaway set screw undergoes increased rotation before failure, then more elements must be experiencing deformation assuming that the plastic strain limit of each element is identical. As more elements experience deformation, then more energy is dissipated plastically.

It is believed that the improved geometries of the present invention act to increase the proportion of the energy that is released as heat from the plastic deformation of the material in the substantially annular groove, thereby reducing the amount of kinetic energy released from the elastic deformation of the metal in the substantially annular groove, and, accordingly, the shock transmitted to the patient and surgeon.

Given the same pre-set shearing torque for the same material with identical bulk and surface properties, the changes in the breakaway area 18 of the screw 2 can influence the energy release behavior of a crack such that the maximum shock released upon breaking/shearing is reduced. In particular, it has been found that the addition of the central hole running through breakaway area 18 greatly reduces the amount of shock released upon breaking/shearing off of the upper head portion 6. While some reduction of the shock released from the addition of the center hole may have been expected, the degree to which the shock was reduced was completely unexpected.

It has been found based on the theory of Linear Elastic Fracture Mechanics (LEFM), that where the stress at the moving crack tip is considered linear elastic with two-dimensional stress, the crack undergoes a rapid, brittle propagation through the structure's thickness when it exceeds a "critical stress intensity." At this critical stress intensity, the energy release rate (G=energy per unit length along the crack tip) of the separating material (potential energy release of the elastic strain) is greater than the crack resistance. The excess of energy becomes kinetic energy which controls the crack tip speed through the material, with the total kinetic energy equal to:

$$E_{kin} = (G-R)da$$

Where: $E_{kin}$: kinetic energy
G: energy release rate
R: crack resistance force.
assuming that: (1) the stress during crack propagation is constant; (2) G is independent of crack speed; and (3) R is constant.

Figure 10:
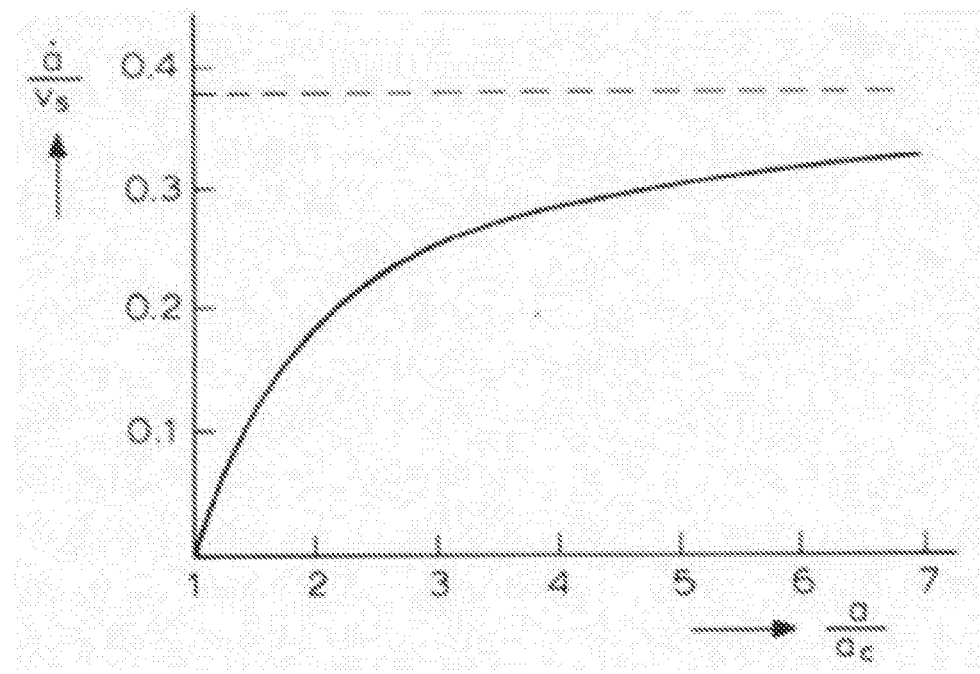
FIG. 10 is a graph showing crack growth rate as a function of crack size.
Figure 11:
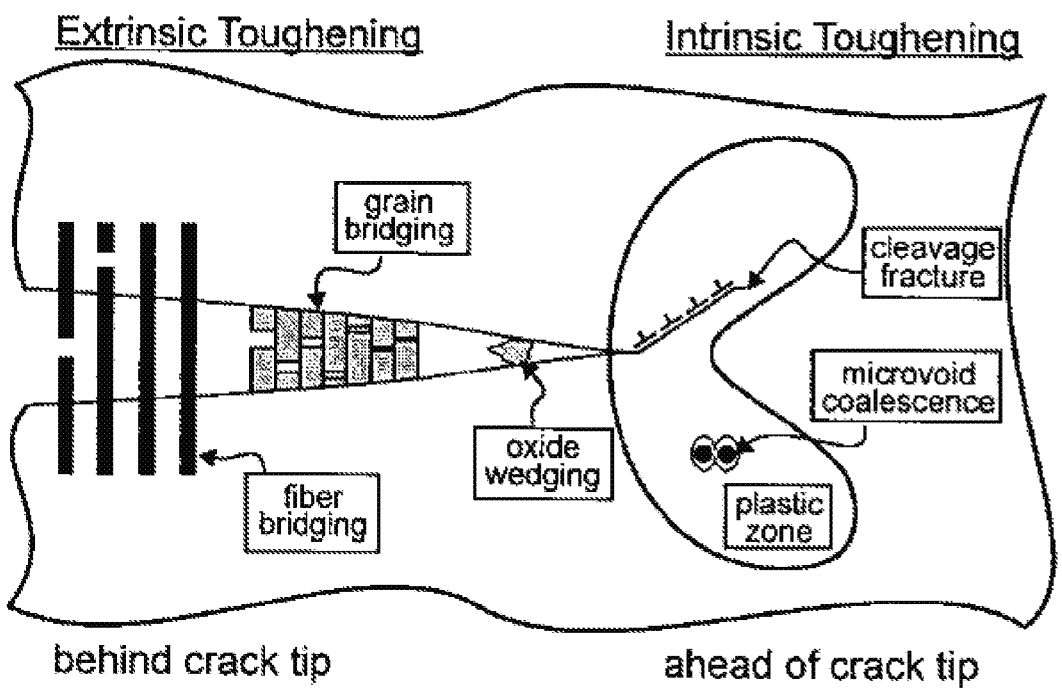
FIG. 11 is an illustration of the competing intrinsic (promoting) and extrinsic (impeding) forces in crack propagation.

Crack resistance and propagation forces are actually a complex combination of a variety of forces, depending on things such as environment, material, and crack/structure geometry. The preceding equation is only a rough guide since, for example, crack resistance does not remain constant, because as crack growth rate is controlled by crack size (FIG. 10) along with other factors. The primary groupings of these forces that influence crack growth are intrinsic and extrinsic as shown in FIG. 11. See, Ritchie, R. O., Gilbert, C. J., & McNaney, J. M. (2000). "Mechanics and mechanisms of fatigue damage and crack growth in advanced materials" International Journal of Solids and Structures 37:311-329, the disclosure of which is incorporated herein by reference. Intrinsic forces stimulate crack growth and are dependent on the material properties, while the extrinsic forces hinder propagation and are primarily a function of crack size/geometry. Ductile materials such as metals predominantly toughen intrinsically, whereas brittle materials toughen through extrinsic forces. Material and process variabilities such as strain rate, strain hardening, surface irregularities, surface processing (e.g. shot peening, electro polishing), and grain structure all affect a part's macroscopic behavior through their influence on the microscopic intrinsic and extrinsic properties.

As a general rule, however, it is clear that: (1) the crack propagation rate increases as the crack grows; (2) crack propagation will become brittle when the growth rate is too fast because R is smaller than the energy release rate, resulting in an abundance of kinetic energy (i.e. shock) and (3) metals primarily toughen due to intrinsic crack initiation forces.

The improved cross sectional geometry of the breakaway area adjacent to the substantially annular groove of the present invention has been found to slow the rate of crack growth thereby dissipating more of the stored energy for plastic deformation and eventually less as shock. In both the thick-wall embodiments (FIGS. 2-4) and tab embodiments (FIGS. 5-7) described above, there are many separate occurrences of shear-separation between the head portion 6 and the lower threaded screw portion 8 compared to prior art the thin-wall breakaway screws that have one singular shear separation. While not being bound to a particular theory, it is believed that the many separation events experienced by breakaway screws according to the present invention are due to the shear-strain being greater at radii further away from the center of torsion. The surfaces in the breakaway region 18 separate first at the radius furthest away from the center of rotation when the ultimate strain is reached, thus making the material just inside this region that separated the new "outer radius". Then the head portion 6 and the lower threaded screw portion 8 must rotate a little more relative to each-other in order for the "new outer radius" to reach ultimate strain, at which point these surfaces separate creating another "new outer radius" just inside of it. It is thought that this keeps happening during successive separation events as the head portion 6 and the lower threaded screw portion 8 continue to rotate relative to each other. And so, when the final separation event happens, there is only a small amount of force acting between the two halves, and there is, therefore, minimal stored elastic energy to be released as shock.

Figure 1B:
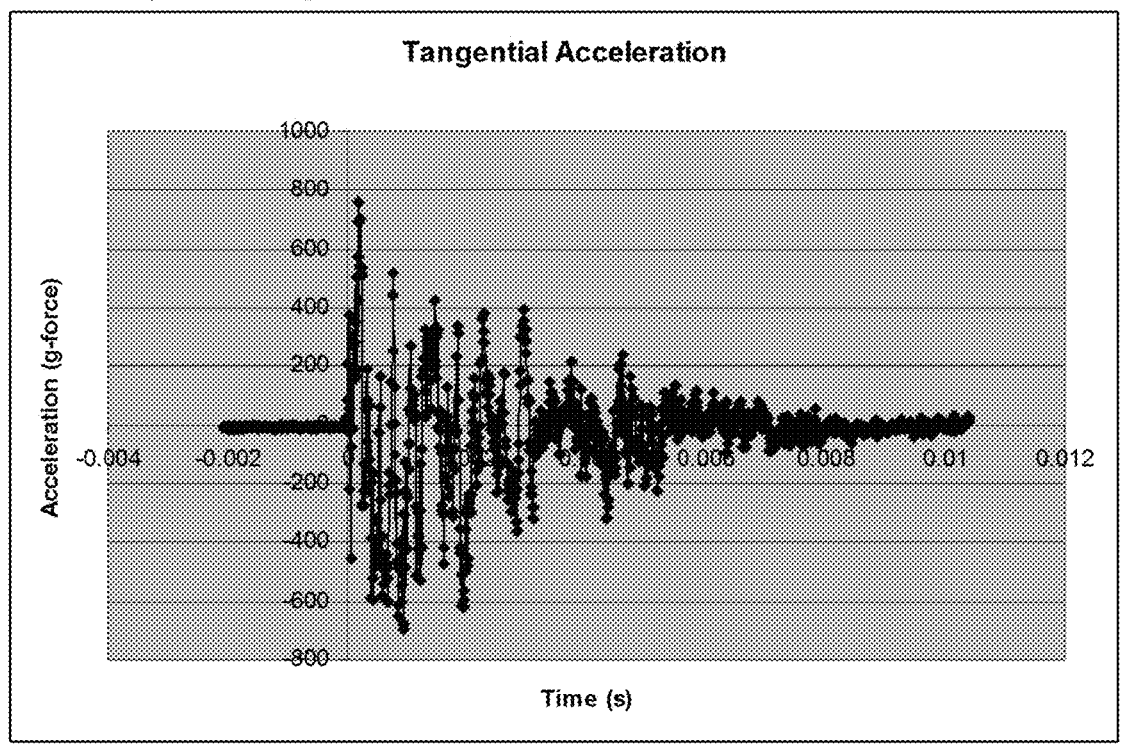
FIG. 1B is a graph of the test data of FIG. 1A wherein the data has been converted to show acceleration (g-forces) per unit time.

By contrast, the prior art thin wall breakaway set screws provide a sudden release of energy as a result of the instantaneous shear failure experienced when the surgeon achieves the designed torque. This is illustrated in FIGS. 1A and 1B by the high acceleration peak at the start of the signal, which indicates that crack initiation and propagation is rapid. This SSBO crack speed, together with the set screw geometry, greatly influence the failure behavior of the prior art set screws, and make the normally ductile material response of the metal become primarily a brittle rupture.

As will be appreciated by those of skill in the art, particularly those in the medical implant community, the breakaway screw designs of embodiments of the present invention changed the mechanical response of the screw during break off (i.e. the shock released) were without changing either the design performance or the material used to make the screw. Embodiments of the present invention provide the advantages of a reduced breakoff shock including, without limitation: reducing the chances of the break off shock causing the pedicle screw breaking through the side of a vertebra or fracturing vertebra or other bone: preventing the reduction the pull out strength of the pedicle screw in the patient that can result from the break off shock, particularly for patients suffering with osteoporosis; decreasing the chance that the tools could slip in the surgeon's hands causing pain or injury to the patient; and prevent premature wear and/or injury to the surgeon's hands caused by the repeated break off shock. These benefits may be obtained using conventional materials and established procedures, such as surgical methods and breakoff torque values.

While the present invention has been described in terms of breakaway set screws for use with medical constructs for the spine and other orthopedic applications, the present invention is not so limited and may be used an other applications where reduced shock break-off is desirable.

EXAMPLES

The following examples are offered to more fully illustrate the invention, but are not to be construed as limiting the scope thereof. Further, while some of examples may include conclusions about the way the invention may function, the inventors do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present.

Example 1

In order to assess the breakaway shock of the reduced shock breakaway screws of embodiments of the present invention and compare it with prior art breakaway screws, from 15 to 17 copies of five different prototypes were machined out of 316L stainless steel. Sample B was a prior art thin-wall design and was used as a first control. Sample A was an alternative thin-wall design. Samples C, D, and E all utilized a solid or thick wall design with a substantially annular groove defining an upper and lower portion and had essentially identical outer dimensions. Sample D utilized the thick wall design as shown in FIG. 2, having a first hole approximately 0.030 inches in diameter drilled along a central axis from the top of the screw to a point approximately one half of the way to the substantially annular groove and a second hole approximately 0.013 inches in diameter drilled along a central axis from the bottom of the first hole and into the lower threaded portion of the screw. Sample E utilized the thick wall design as shown in FIG. 3, having a central hole approximately 0.030 inches in diameter drilled from the top of the screw along a central axis and into the lower threaded portion of the screw. Sample C was essentially the same as Samples D and E, but without the central hole and was used as a second control. Samples A-E were all designed to break off at essentially the same predetermined torque value.

Materials

1× machine lathe
1× laptop computer running TracerDAQ Pro software (Measurement Computing Corporation (Norton, Mass.))
1× analogue to digital converter (USB-1608GX) Measurement Computing Corporation (Norton, Mass.)
1× ProjectBoard with an operational-amplifier construct (350 gain, CMRR 130 dB)
1× accelerometer (Model 8728A500 500 g-force K-Shear Accelerometer (Kistler Group, (Winterthur, Switzerland))
1× accelerometer power supply/coupler with SNC cable output (Model No. 511882 (Kistler Group (Winterthur, Switzerland))
1× accelerometer fixture (Custom designed & created by Machine Tek Systems)
1× allen wrench to tighten set-screws of accelerometer fixture
1×TQM201-56.5 torque sensor (Omega Engineering, Inc. (Stanford, Conn.) (See http://www.omega.com/Pressure/pdf/TQ201.pdf)
1× Trantorque (Mini #6202107) bushing (Fenner Drives, Inc. (Manheim, Pa.))
1× ⅝ box wrench for Trantorque tightening
1×SSBO breaking tool (Medtronics, Inc. (Minneapolis, Minn.))
15× 5 prototypes (75 total pieces)

Set-Up and Methods

The standard surgeon tool was used to shear off the hex head exactly like in the current surgery procedure. However, the counter-torque tool was not needed due to the prototype piece being rigidly held by a lathe chuck. Also, the tool was used in a horizontal direction rather than the vertical direction that a surgeon usually operates on a person. The tool was still used co-axial to the test piece, so this difference should have had a negligible effect on the results.

The interior of the TranTorque bushing was roughed with an available cutting-tool and the surface of the circular end of each sample was roughed with ScotchBrite, and the debris wiped off with a clean rag. The TranTorque was set into the torque sensor and the torque sensor was secured into the machine lathe chuck and the accelerometer laid out.

The torque sensor leads were connected to the input side of an (350 gain) operational amplifier (op-amp), and the output of this op-amp was fed into the data acquisition unit (DAQ). The accelerometer signal was feed into a signal conditioning box which output into the same DAQ. The torque sensor values and accelerometer values were both recorded by the same DAQ unit so that extra manual work was not needed to synchronize two different signals The DAQ unit then fed into a computer running TracerDAQ Pro software.

The circular end of each sample was then secured into the TranTorque using a box-wrench and moderating the tightening force by only using the thumb (~150 in-lbs, 17 Nm). There were no concerns about this torque causing pre-stress in the failure region because there was nothing holding the other end of the sample.

The computer was placed on a cart adjacent to the lathe. The TracerDaqPRO software was used to collect the DAQ signal. The software was only capable of making and recording 1,000K readings (i.e. 4 seconds at 250 kHz). Accordingly, the software was set to read 2 channels at 250 kHz for 2 seconds. The triggering function of the software was set to the "Torque" channel and for a signal rising past 0.5V (3.67 Nm, 32.5 in-lbf). This triggering scheme ensured that data collection began only when significant intentional force was applied, ensuring the maximum torque value was captured.

On the circular (and stationary) side of the test piece, the accelerometer was attached to the shaft using set-screws in a custom fixture. The accelerometer was positioned away from the breakoff region so as to minimize the influence from any microscopic failure behavior, but was always the same distance away from the rigidly held TranTorque in order to remain distinctly separate from that structure.

The handle of the break-off tool was then used to engage the hexagonal upper portion of each sample and then rotated clockwise, while remaining co-axial with the secured prototype piece until the sample broke. The torque-force history was recorded at the same time as the accelerometer data, and each breakoff event was saved as a separate file for later analysis. (See FIG. 12)

Results

Figure 12:
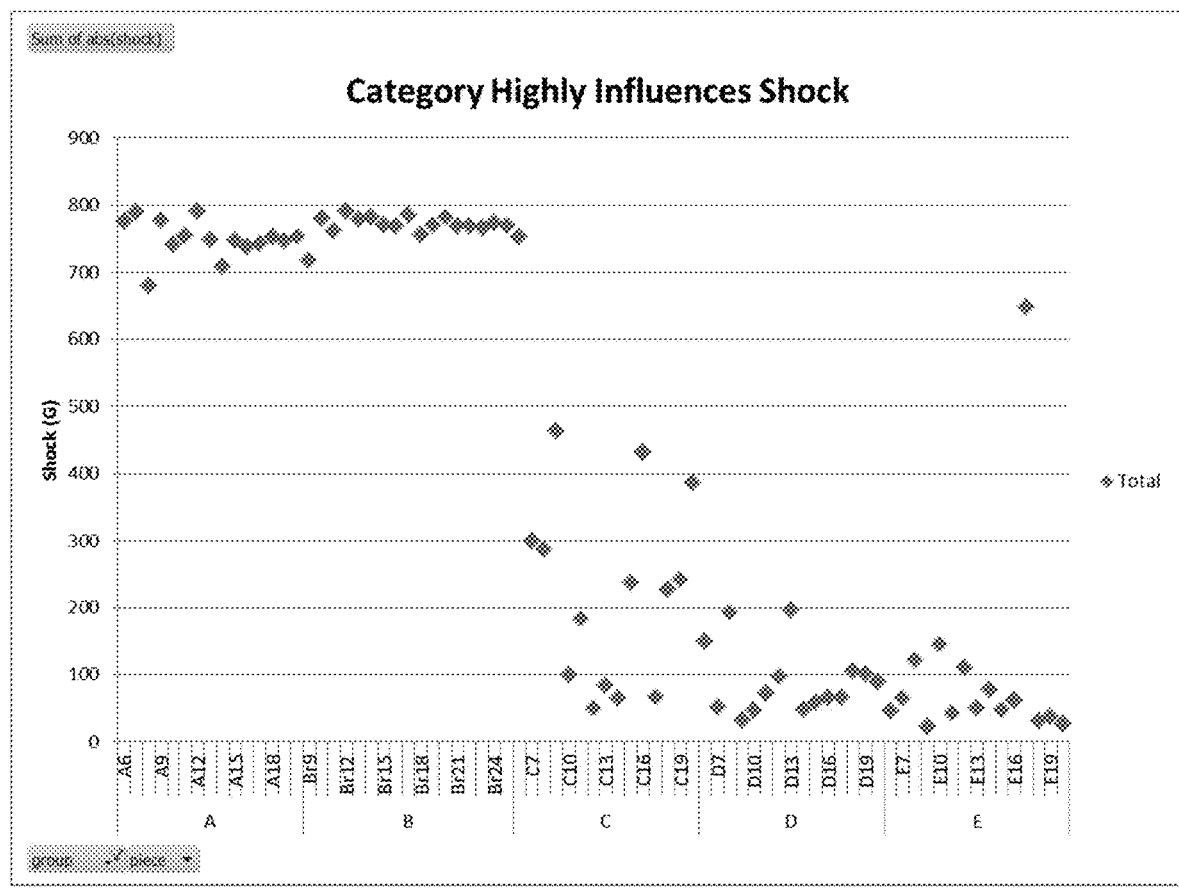
FIG. 12 is a graph showing the results of break off tests conducted on reduced shock screw according to one or more embodiments of the present invention.

The results of these tests are reported on Table 1 below and graphically represented in FIG. 12.

TABLE 1

|  | A | B | C | D | E |
|---|---|---|---|---|---|
| Average Shock | 750 g | 773 g | 259 g | 92 g | 102 g |
| Shock reduction based upon Sample A |  | 3% | 66% | 88% | 89% |
| Shock reduction based upon Sample B | none | X | X | 65% | 60% |
| Surgeon feedback (scale of 1-10 for shock) | 9 | 10 | 4 | 1 | 1 |

As can be seen, Samples D and E had significantly reduced average shock (measured in multiples of the force of gravity "g") compared to either control. The design used for Sample D recorded an 88% reduction in the average shock compared to the thin wall control (Sample B) and a 65% reduction in the average shock compared to the solid control (Sample C). Similarly, the design used for Sample E recorded an 89% reduction in the average shock compared to the thin wall control (Sample B) and a 60% reduction in the average shock compared to the solid control (Sample C). And for Sample E, it is believed that the results reported in Table 1 are likely skewed downward by the results for a single sample that appears to be an outlier. Without this value, the average reduction in shock was 92% compared to Sample B (thin walled control) and 76% compared to Sample C (the solid wall control).

Example 2

A 4 level fusion (5 pedicle screws) construct was installed into a bone block. Pilot holes were drilled into the bone block with an electric drill, and the pedicle screw posts were installed using a 3 mm driver attached to an electric drill. An electric drill was used for these operations to reduce the influence of wobble, and therefore reduce any effect that a construct's rigidity has on the SSBO shock and die-down characteristics.

The samples were randomly assigned and placed in the 4 level fusion (5 pedicle screws) construct, and the surgeon was asked to break off each sample and provide subjective feedback after all of the sample had been broken off. The test surgeon ranked the samples by severity of break-off shock (1-10, with 1 being the least shock).

The results are reported on Table 2 and indicate a significant reduction in the subjective break off shock for samples D and E, compared to the other Samples.

TABLE 2

|  | A | B | C | D | E |
|---|---|---|---|---|---|
| Surgeon feedback (scale of 1-10 for shock) | 9 | 10 | 4 | 1 | 1 |

Moreover, these results largely track the results shown in Table 1, in Example 1 above.

In light of the foregoing, it should be appreciated that the present invention significantly advances the art by providing a reduced shock breakaway screw that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A reduced shock breakaway screw comprising:
an upper head portion, said upper head portion having an upper end and a lower end, at least said lower end having a rectangular cross sectional area and being configured to mate with a first torque applying device, wherein said upper head portion passes through a central axis of the reduced shock breakaway screw and has a first and second side and a first and second end, with the distance between said first and second ends defining a length and the distance between said a first and second sides defining a width;
a lower threaded screw portion connected to said upper head portion and having at least one of a first recessed opening on a first side of said upper head portion and a second recessed opening on a second side of said upper head portion, wherein at least one of the first and second recessed openings is configured to mate with a second torque applying device while said upper head portion is connected to said lower threaded screw portion;
a first groove running along a bottom edge of the bottom end on the first side of said upper head portion; and
a second groove running along a bottom edge of the bottom end on the second side of said upper head portion; said first and second grooves defining a breakaway area;
wherein said upper head portion will separate from said lower threaded screw portion upon application of a predetermined torque to said upper head portion.

2. The reduced shock breakaway screw of claim 1 wherein said lower threaded screw portion engages the second torque applying device in such a way as to permit the second torque applying device to apply torque to said lower threaded screw portion without applying significant torque to said upper head portion.

3. The reduced shock breakaway screw of claim 1 further comprising a hole running transverse to said central axis between said first and second grooves and passing through the central axis of said reduced shock breakaway screw.

4. The reduced shock breakaway screw of claim 1 wherein the breakaway area has a substantially hour glass shape when viewed in horizontal cross section with its narrowest point at or near the central axis of said reduced shock breakaway screw.

5. The reduced shock breakaway screw of claim 4 further comprising a hole running transverse to said central axis between said first and second grooves and passing through the central axis of said reduced shock breakaway screw.

6. The reduced shock breakaway screw of claim 1 wherein said lower threaded screw portion is configured to be received in a threaded bore of a surgical construct for use with one or more bones of a patient.

7. The reduced shock breakaway screw of claim 1 further comprising a center hole running along the central axis of said reduced shock breakaway screw from the top of said upper head portion through said breakaway region and to or into said lower threaded screw portion.

\* \* \* \* \*